United States Patent
Hu

(10) Patent No.: US 10,765,333 B2
(45) Date of Patent: Sep. 8, 2020

(54) SYSTEM THAT ASSESSES HEALTH CONDITION BY MEASURING PULSE AND METHOD OF ASSESSING THE SAME

(71) Applicant: Zhao Qi Hu, Tokyo (JP)

(72) Inventor: Zhao Qi Hu, Tokyo (JP)

( * ) Notice: Subject to any disclaimer, the term of this patent is extended or adjusted under 35 U.S.C. 154(b) by 0 days.

(21) Appl. No.: 16/438,722

(22) Filed: Jun. 12, 2019

(65) Prior Publication Data

US 2020/0146570 A1    May 14, 2020

(30) Foreign Application Priority Data

Nov. 8, 2018    (JP) .................................. 2018-210210

(51) Int. Cl.
*A61B 5/024*    (2006.01)
*A61B 5/00*    (2006.01)
*A61B 5/022*    (2006.01)

(52) U.S. Cl.
CPC ........ *A61B 5/02438* (2013.01); *A61B 5/0004* (2013.01); *A61B 5/0022* (2013.01);
(Continued)

(58) Field of Classification Search
CPC .................... A61B 5/024–0255; A61B 5/4854
See application file for complete search history.

(56) References Cited

U.S. PATENT DOCUMENTS

2003/0212335 A1* 11/2003 Huang ................... A61B 5/021
600/500

2007/0010749 A1* 1/2007 Meng ................. A61B 5/02116
600/490
(Continued)

FOREIGN PATENT DOCUMENTS

CN    103190890 A    7/2013
CN    104083147 A    10/2014
(Continued)

OTHER PUBLICATIONS

Dharmananda, Subhuti. "The Significance of Traditional Pulse Diagnosis in the Modern Practice of Chinese Medicine." Aug. 2000. http://www.itmonline.org/arts/pulse.htm (Year: 2000).*
(Continued)

*Primary Examiner* — Meredith Weare
(74) *Attorney, Agent, or Firm* — Westerman, Hattori, Daniels & Adrian, LLP

(57) ABSTRACT

A system that assesses health condition by measuring pulse includes: a pulse measuring device that measures an artery of a user who receives assessment of health condition; a terminal that has a function that transmits measured-value data on pulse measured by the pulse measuring device to a health assessing administrator and receives information from the health assessing administrator; an administrative server that is administered by the health assessing administrator, analyzes the measured-value data transmitted from the terminal, and stores various data on health condition that is necessary to assess and analyze health condition. The user transmits the measured-value data on measured pulse from the terminal to the health assessing administrator, and the health assessing administrator transmits assessment information on health condition analyzed by the administrative server to the terminal.

7 Claims, 10 Drawing Sheets

(52) U.S. Cl.
CPC ...... *A61B 5/02233* (2013.01); *A61B 5/02444* (2013.01); *A61B 5/4854* (2013.01); *A61B 5/681* (2013.01); *A61B 5/6843* (2013.01); *A61B 2562/0247* (2013.01); *A61B 2562/06* (2013.01)

(56) References Cited

U.S. PATENT DOCUMENTS

| | | | |
|---|---|---|---|
| 2008/0235058 A1 | 9/2008 | Friedman et al. | |
| 2009/0124914 A1* | 5/2009 | Kuo | A61B 5/02116 600/500 |
| 2009/0204668 A1* | 8/2009 | Huang | G06F 19/3456 709/203 |
| 2010/0022895 A1* | 1/2010 | Kim | A61B 5/024 600/485 |
| 2010/0286538 A1* | 11/2010 | Kim | A61B 5/0225 600/493 |
| 2013/0046191 A1* | 2/2013 | Lin | A61B 5/02141 600/500 |
| 2013/0303923 A1* | 11/2013 | Lerner | A61B 5/02208 600/492 |
| 2016/0058393 A1* | 3/2016 | Mi | A61B 5/0255 600/501 |
| 2016/0331246 A1* | 11/2016 | Chen | A61B 5/024 |
| 2017/0105628 A1* | 4/2017 | Cheng | A61B 5/02108 |
| 2017/0258336 A1* | 9/2017 | Furness, III | A61B 5/026 |
| 2019/0014996 A1* | 1/2019 | Qian | A61B 5/02108 |
| 2019/0046050 A1* | 2/2019 | Kato | A61B 5/022 |

FOREIGN PATENT DOCUMENTS

| | | |
|---|---|---|
| CN | 105411542 A | 3/2016 |
| CN | 108158563 A | 6/2018 |
| JP | 63-305838 A | 12/1988 |
| JP | 2017-153622 A | 9/2017 |

OTHER PUBLICATIONS

Chen et al. "A Non-Contact Pulse Automatic Positioning Measurement System for Traditional Chinese Medicine." Sensors 2015, 15, 9899-9914. (Year: 2015).*

Decision to Grant a Patent dated Jan. 17, 2019, issued in counterpart Japanese Patent Application No. 2018-210210, w/English translation (5 pages).

Notification of Reasons for Refusal dated Dec. 12, 2018, issued in counterpart Japanese Patent Application No. 2018-210210, w/English translation (8 pages).

* cited by examiner

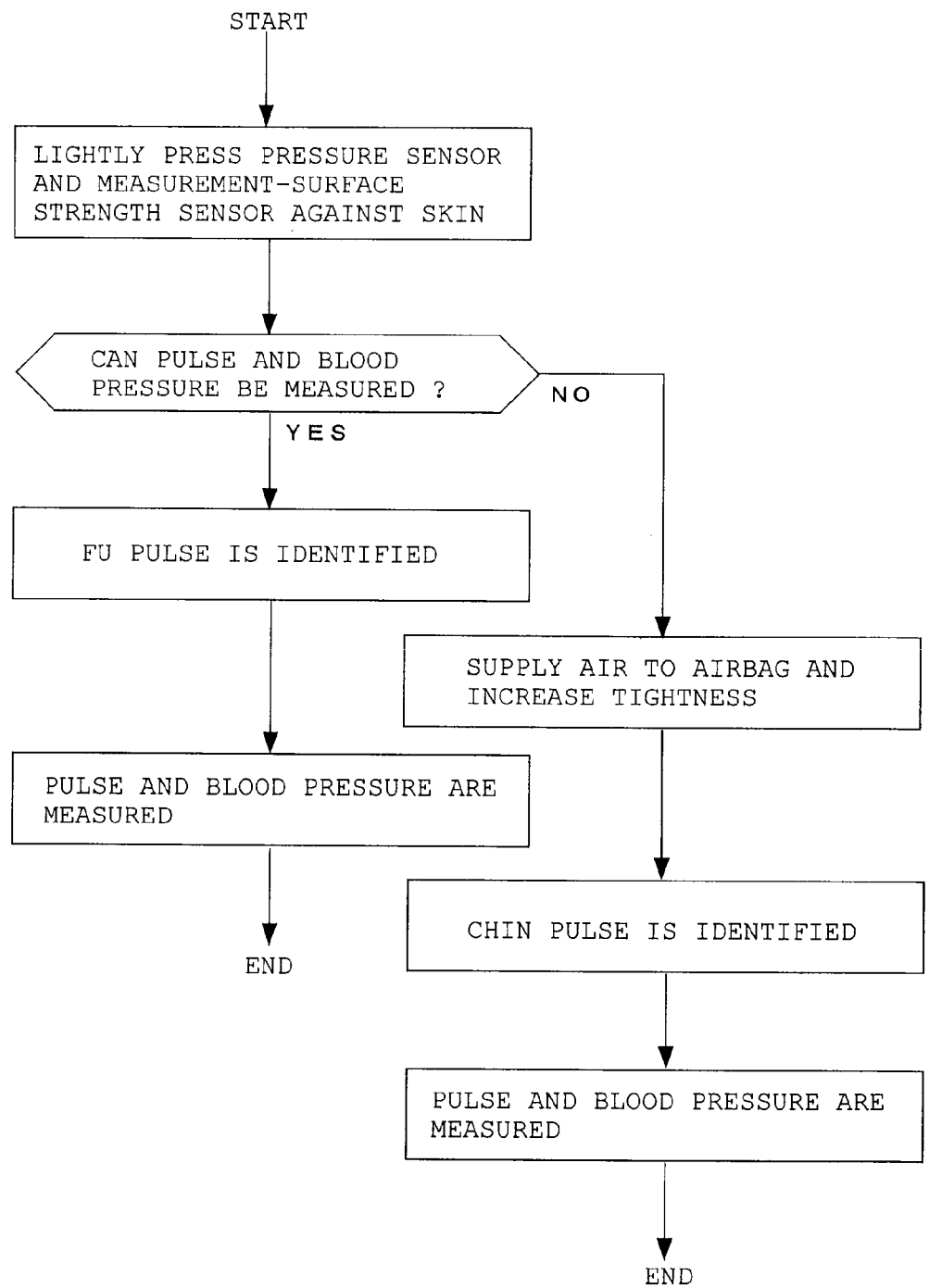

FIG. 12A  DEPTH OF PULSE
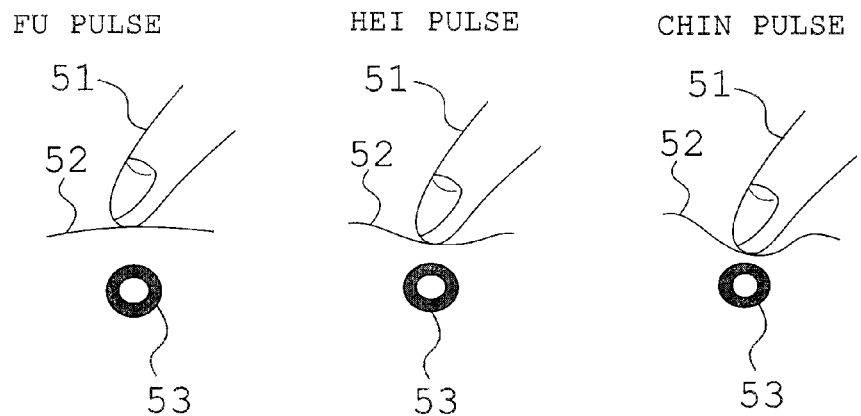
FIG. 12B  SPEED OF PULSE
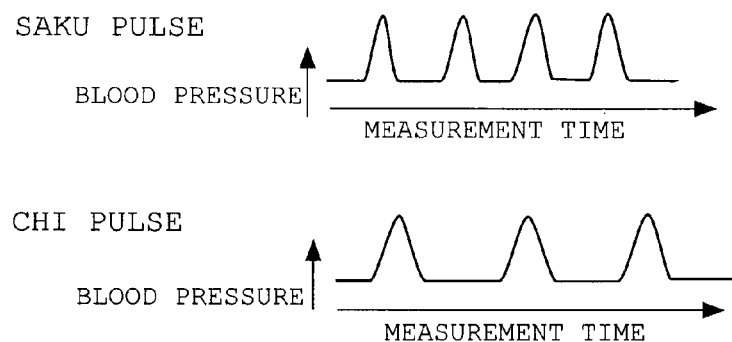
FIG. 12C  STRENGTH OF PULSE
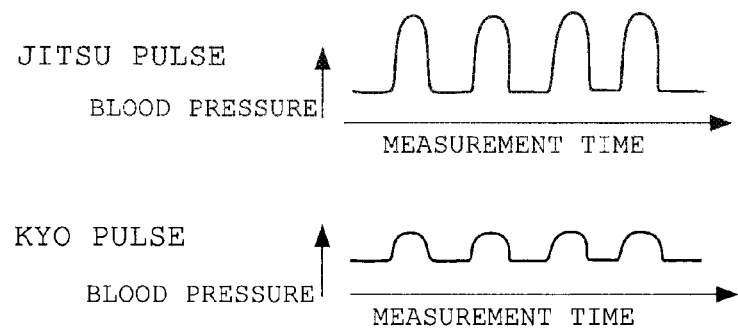

SYSTEM THAT ASSESSES HEALTH CONDITION BY MEASURING PULSE AND METHOD OF ASSESSING THE SAME

BACKGROUND

Technical Field

The present invention relates to a technique that assesses health condition (physical condition) of a person by measuring pulse of the person, and relates to a system that assesses health condition by measuring pulse and a method of operating the same. The system delicately assesses health condition of a person by measuring pulse of an artery at a wrist and analyzing measured numerical data.

Related Art

There are conventional methods in which pulse of a person is measured and health condition of the person is known. A person has a difference in pulse between during rest and during exercise. Further, pulse varies by physical condition during a day. Heart disease or disease of viscera is sometimes found using the method. Pulse is an index of health condition of a person. A human heart repeatedly beats in a regular rhythm and pumps blood throughout a body. A human heart beats about a hundred thousand times a day. The beats reach arteries, such as an artery at a wrist, and become pulse. Source of the beats is electrical stimulus generated in a sinus node within a heart. The electrical stimulus repeatedly makes heart muscles contract and relax and generates beats.

A healthy adult has a pulse of about 50 to 100 times (beats) per minute during rest. Pulse of a person becomes fast when the person exercises or becomes nervous. On the other hand, pulse of a person becomes slow when the person sleeps or relaxes. Knowing condition of pulse contributes to health care.

To know human health condition, oriental medicine uses a method "pulse diagnosis" to take pulse and infer human physical condition. The reason is that variation of pulse is delicately related to physical condition. As illustrated in FIG. 11, in the pulse diagnosis of traditional oriental medicine, three fingers (forefinger, middle finger, and ring finger) are pressed against a wrist to infer physical condition. Fingertips touch a "shaku" position, a "kan" position, and a "sun" position of a measured wrist (a left hand in FIG. 11) that faces upward. The "shaku" position, the "kan" position, and the "sun" position align in this order, and the "shaku" position is the lowest position. An expert measures pulse by feeling pulse on fingers of the expert at the respective positions. The expert judges health condition by measuring pulse at six positions of both wrists. The expert infers physical condition (health condition) of the person by measuring a balance of pulse which the three fingers feel, and quality of beats.

In a method used to infer human physical condition in the "pulse diagnosis", condition of an artery is measured by pressing fingers against skin at a wrist, for example, as illustrated in FIGS. 12A, 12B, and 12C. "Depth", "speed", and "strength" of pulse are mainly measured.

There are three ways of taking pulse to measure the "depth" of pulse, as illustrated in FIG. 12A. One of the three ways of taking pulse is called "fu pulse" or "fu taking". In case of the "fu pulse", a finger 51 of an expert slightly touches skin 52. One of the three ways of taking pulse is called "hei pulse" or "middle taking". In case of the "hei pulse", a finger 51 of an expert a little strongly touches skin 52. One of the three ways of taking pulse is called "chin pulse" or "chin taking". In case of the "chin pulse", a finger 51 of an expert more strongly touches skin 52.

As to the "speed" of pulse, fast pulse is called "saku pulse", as illustrated in FIG. 12B. Slow pulse is called "chi pulse". People individually have large differences in the "speed" of pulse. Therefore, standards need to be fixed for each person to judge the "speed".

As to the "strength", when a fingertip strongly feels beats, pulse is strong and is called "jitsu pulse", as illustrated in FIG. 12C. Weak pulse is called "kyo pulse". People individually have large differences in the "strength" of pulse. Therefore, standards need to be fixed for each person to judge the "strength".

As illustrated in FIG. 11, in pulse diagnosis of oriental medicine, three fingers: a forefinger, a middle finger, and a ring finger are pressed against an artery of a left wrist and an artery of a right wrist to perform measurement. Health condition of human viscera, especially condition of five viscera (heart, liver, spleen, lung, and kidney) is inferred based on pulse at positions on left and right wrists where the fingers touch. Condition of a heart and a small intestine is inferred based on pulse of an artery at a "sun" position of a left wrist. The "sun" position is the nearest to fingertips. Condition of a liver and a gallbladder is inferred based on pulse of the artery at a "kan" position next to the "sun" position of the left wrist. Condition of a kidney and a bladder is inferred based on pulse of the artery at a "shaku" position next to the "kan" position of the left wrist.

Condition of a lung and a large intestine is inferred based on pulse of an artery at a "sun" position of a right wrist. The "sun" position is the nearest to fingertips. Condition of a spleen and a stomach is inferred based on pulse of the artery at a "kan" position next to the "sun" position of the right wrist. Condition of a viscus near the kidney (vigor of the kidney (san shou)) is inferred based on pulse of the artery at a "shaku" position next to the "kan" position of the right wrist.

In this way, health condition of five viscera of a person is assessed by measuring pulse at wrists. However, it is actually difficult to determine slight differences by measuring pulse. Therefore, ability of experts is largely relied upon. Therefore, a technique that measures pulse with a measuring device is proposed. For example, JP S63-305838 A, "pulse meter", proposes a pulse meter that includes an arm fixing rest on which a forearm is disposed with a radial-artery portion facing upward, a pulse detector that is in contact with the radial-artery portion, a pulse-detector support that moves the pulse detector up or down and applies a desired pressing force to the pulse detector, a first pipe that includes a first pressure sensor at one end, and a middle portion that is connected to a transmission tube that connects to the pulse detector, a second pipe that includes a second pressure sensor at one end, and includes a second three-way switching valve and a check valve arranged in this order from the one end to the other end, a pump that is upstream from a connection point between the first pipe and the second pipe, and is connected to the connection point through a first three-way switching valve, and a display unit that displays differences between output signals from the first pressure sensor and output signals from the second pressure sensor.

SUMMARY

According to the pulse meter disclosed in JP S63-305838 A, a radial-artery portion does not move since a forearm is disposed on the fixing rest. Further, a desired pressing force is applied to the pulse detector that is in contact with the radial-artery portion. Therefore, "fu pulse", "hei pulse", and "chin pulse" are delicately changed. The delicate differences are determined, and health condition of a heart, a liver, a kidney, a lung, a spleen, and vigor of the kidney (san shou) is inferred. However, health condition is not correctly assessed based on the measurement result without directly consulting a traditional Chinese medicine doctor or an expert who has deep knowledge in oriental medicine, such as an acupuncturist.

In other words, measurement is performed, but health condition is not assessed.

The present inventor focuses on a fact that excellent assessment of health condition of oriental medicine called "pulse diagnosis" as described above is automatically performed by preliminarily storing various information that allows assessing health condition based on pulse in a database. There is no need to directly consult a traditional Chinese medicine doctor and an expert who has deep knowledge in oriental medicine, such as an acupuncturist. The present inventor thinks that the database for pulse is collectively administered, and data of the database is used by a plurality of people, and thus health condition of the plurality of people is assessed using "pulse diagnosis".

The present inventor also thinks that an inventive device applied to a pulse measuring device allows a delicate position where pulse is measured to be easily discovered without relying upon an expert, and measurement with a sensor allows pulse to be delicately measured similarly as delicate touch of fingertips that measure pulse.

The present invention is made to solve the above problems. That is, an object of the present invention is to provide a system that assesses health condition by measuring pulse that allows "pulse diagnosis" that has been performed by traditional Chinese medicine doctors or experts, such as acupuncturists by performing touch diagnosis to be performed with a pulse measuring device and database analysis. Consequently, health condition is accurately assessed, and health care is performed. Further, health condition is assessed based on both the assessment of health condition and general health checkup. Therefore, the system that assesses health condition by measuring pulse contributes to health care. Another object of the present invention is to provide a method of operating the system that assesses health condition by measuring pulse.

A system that assesses health condition by measuring pulse, and more specifically, assesses health condition of a person by measuring pulse of the person and analyzing measured numerical data, according to an aspect of the present invention, includes:

a pulse measuring device (2b) that measures pulse and blood pressure at an artery of a user (A) who receives an assessment of health condition;

a terminal (1) that includes a display unit (13) that displays measured-value data measured by the pulse measuring device (2b), a controlling unit (12) controlled by operating an input unit (14), a transmitting and receiving unit (11) that transmits the measured-value data to a health assessing administrator (B) and receives information from the health assessing administrator (B); and an administrative server (3) that is administered by the health assessing administrator (B), and includes a transmitting and receiving unit (32) that receives the measured-value data transmitted from the terminal (1), a measured-value-information database (36) that stores data on previously-measured pulse of the user (A), a health-condition-information database (37) that stores data on relation between unhealthy viscera and positions where pulse is measured, and a determining unit (34) that assesses and analyzes health condition, and the user (A) transmits the measured-value data on measured pulse from the terminal (1) to the health assessing administrator (B), and the health assessing administrator (B) transmits assessment information on health condition analyzed by the administrative server (3) to the terminal (1), and the pulse measuring device (2b) includes:

a band (21) worn around a portion that corresponds to a radial-artery portion (ar) on a wrist (wr);

three airbags (23) inflated by air supplied by a pump (22) attached to the band (21);

guide sheets (24) that are attached to the respective airbags (23), and each have a curved shape;

pressure sensors (25) that are disposed via the respective guide sheets (24) on the respective airbags (23), and measure pulse; and measurement-surface strength sensors (27) that are disposed near the respective pressure sensors (25) and measure strength of pressing force that presses the respective pressure sensors (25) against a surface of skin (sk) of a wrist (wr), and three positions in the radial-artery portion (ar) of the wrist: a "sun" position near fingertips, a "kan" position next to the "sun" position, and a "shaku" position next to the "kan" position are individually measured.

In the system that assesses health condition by measuring pulse according to an aspect of the present invention, the measured-value-information database (36) of the administrative server (3) stores measured-information data on a current age of the user (A), maximum and minimal pulse rates and maximum and minimal blood pressures of the user (A) when the user (A) is healthy, a medical history of the user (A), an age of the user (A) at a time of disease, and maximum and minimal pulse rates and maximum and minimal blood pressures of the user (A) at the time of disease, and the health-condition-information database (37) of the administrative server (3) stores information data on relation between viscera, pulse rates at positions where pulse is measured, and maximum and minimal blood pressures of healthy ordinary people classified according to age, and information data on relation between viscera, pulse rates at positions where pulse is measured, and maximum and minimal blood pressures of ordinary people when ordinary people are unhealthy.

In the system that assesses health condition by measuring pulse according to an aspect of the present invention, the pulse measuring device (2b) is configured so that the measurement-surface strength sensors (27) that are disposed near the respective pressure sensors (25) and measure strength of pressing force that presses the respective pressure sensors (25) against a surface of skin (sk) of a wrist (wr) each measure a difference between "fu pulse" mainly felt by lightly pressing a finger against a radial artery and "chin pulse" felt by strongly pressing a finger against a radial artery.

It is preferable that two arrows (26) are marked on a surface of the band (21) of the pulse measuring device (2b), and a central portion of the pressure sensor (25) is on a line (L) that passes through the two arrows (26).

A method of operating a system that assesses health condition by measuring pulse, and more specifically, includes an administrative server (3), and analyzes numerical data of measured pulse of a person to assess health condition of the person according to an aspect of the present invention, includes:

measuring pulse and blood pressure of an artery of a user (A) who receives an assessment of health condition with a pulse measuring device (2b);

transmitting measured-value data on measured pulse of the user (A) from a terminal (1) that includes a controlling unit (12) controlled by operating an input unit (14) to the administrative server (3) of a health assessing administrator (B);

comparing, by means of a determining unit (34), the measured-value data, such as a pulse rate and a blood pressure, transmitted from the user (A) with a measured-value-information database (36) of the administrative server (3) that stores data on previously-measured pulse of the user (A), and a health-condition-information database (37) of the administrative server (3) that stores data on relation between unhealthy viscera and positions where pulse is measured;

assessing and analyzing health condition of the user (A) in such a manner that when pulse of the measured-value data mainly on measured pulse of the user (A) is pulse that has 90 beats/minute or more and is called "saku pulse", condition in which blood flow is fast, and condition in which basal metabolic rate increases are indicated, and thus suspicion of general infections, such as febrile illness, mental tension, hyperthyroidism, and dehydration, is indicated, or when pulse of the measured-value data is pulse that has 60 beats/minute or less and is called "chi pulse", condition in which blood flow is slow, and condition in which basal metabolic rate decreases are indicated, and thus suspicion of hypothyroidism or hypothermia is indicated; and transmitting an analysis result of health condition to the terminal (1) of the user (A).

The method of operating a system that assesses health condition by measuring pulse according to an aspect of the present invention, may further include:

operating the system that assesses health condition in such a manner that when pulse of the measured-value data on measured pulse of the user (A) has abnormality of an artery of a left wrist at a position called a "sun" position near fingertips, the system that assesses health condition determines that a heart and a small intestine have abnormality, when pulse of the measured-value data on measured pulse of the user (A) has abnormality of an artery of a left wrist at a position called "kan" position next to the "sun" position, the system that assesses health condition determines that a liver and a gallbladder have abnormality, when pulse of the measured-value data on measured pulse of the user (A) has abnormality of an artery of a left wrist at a position called "shaku" position next to the "kan" position, the system that assesses health condition determines that a kidney and a bladder have abnormality, when pulse of the measured-value data on measured pulse of the user (A) has abnormality of an artery of a right wrist at a "sun" position, the system that assesses health condition determines that a lung and a large intestine have abnormality, when pulse of the measured-value data on measured pulse of the user (A) has abnormality of an artery of a right wrist at a "kan" position, the system that assesses health condition determines that a spleen and a stomach have abnormality, and when pulse of the measured-value data on measured pulse of the user (A) has abnormality of an artery of a right wrist at a "shaku" position, the system that assesses health condition determines that a viscus near the kidney (vigor of the kidney (san shou)) has abnormality.

According to a system that assesses health condition structured as described above and a method of operating the same, a user (A) transmits measured-value data on measured pulse from a terminal (1) to a health assessing administrator (B), and the health assessing administrator (B) who has received the measured-value data transmits assessment information on health condition analyzed by an administrative server (3) to the terminal (1).

Consequently, a plurality of people receives assessment of health condition based on pulse diagnosis that has conventionally needed ability of experts, and do not need to consult an expert. A user (A) receives an assessment of health condition by only measuring pulse of wrists of the user (A) in home, for example.

According to a system that assesses health condition and a method of operating the same according to an aspect of the present invention, a user (A) delicately knows health condition (physical condition) based on both an assessment of the system and a result of health checkup, such as comprehensive medical checkup.

According to a system that assesses health condition and a method of operating the same according to an aspect of the present invention, "depth", "speed", "strength", and "position" of pulse are measured in addition to measurement of pulse and blood pressure of an artery. Therefore, health condition is known in detail. In measurement, a forefinger, a middle finger, and a ring finger are pressed against an artery of a left wrist and an artery of a right wrist. Health condition of human viscera, especially condition of five viscera (heart, liver, spleen, lung, and kidney) is inferred based on pulse at positions on left and right wrists where fingers touch. Condition of a heart is inferred based on pulse of an artery at a "sun" position of a left wrist. Condition of a liver is inferred based on pulse of the artery at a "kan" position next to the "sun" position of the left wrist. Condition of a kidney is inferred based on pulse of the artery at a "shaku" position next to the "kan" position of the left wrist. Condition of a lung is inferred in detail based on pulse of an artery at a "sun" position of a right wrist. The "sun" position is near fingertips. Condition of a spleen is inferred in detail based on pulse of the artery at a "kan" position next to the "sun" position of the right wrist. Condition of a viscus near the kidney (vigor of the kidney (san shou)) is inferred in detail based on pulse of the artery at a "shaku" position next to the "kan" position of the right wrist.

According to an aspect of the present invention, transmission and receipt between a person at a remote place and a health assessing administrator (B) allows health condition of the person to be known. A system that assesses health condition and a method of operating the same according to an aspect of the present invention allow easily assessing whether victims in a stricken area are in emergency or not. For example, a victim measures pulse of arms of the victim. The victim transmits measured-value data from a terminal (1) to a health assessing administrator (B). The victim receives assessment of health condition. Consequently, assessment whether the victim needs to be immediately rescued is possible. Therefore, life of many people is saved.

BRIEF DESCRIPTION OF DRAWINGS

FIG. 2A is a front view, and FIG. 2B is a side cross-sectional view;

FIG. 3 is a flowchart that illustrates control in which a measurement-surface strength sensor of the pulse measuring device adjusts tightness of a band;

FIG. 4A is a front view, and FIG. 4B is a side cross-sectional view;

FIGS. 12A to 12C are a schematic explanation view that illustrates a measurement method of pulse diagnosis of oriental medicine in which a finger is pressed against skin to measure an artery, "depth" of pulse is measured in FIG. 12A, "speed" of pulse is measured in FIG. 12B, and "strength" of pulse is measured in FIG. 12C.

DETAILED DESCRIPTION

A system that assesses health condition by measuring pulse according to an aspect of the present invention is a system that assesses health condition (physical condition) of a person by measuring pulse of the person at wrists and analyzing measured numerical data.

Embodiment 1

Hereinafter, an embodiment of the present invention will be described with reference to the drawings.

<Configuration of System that Assesses Health Condition>

Figure 1:
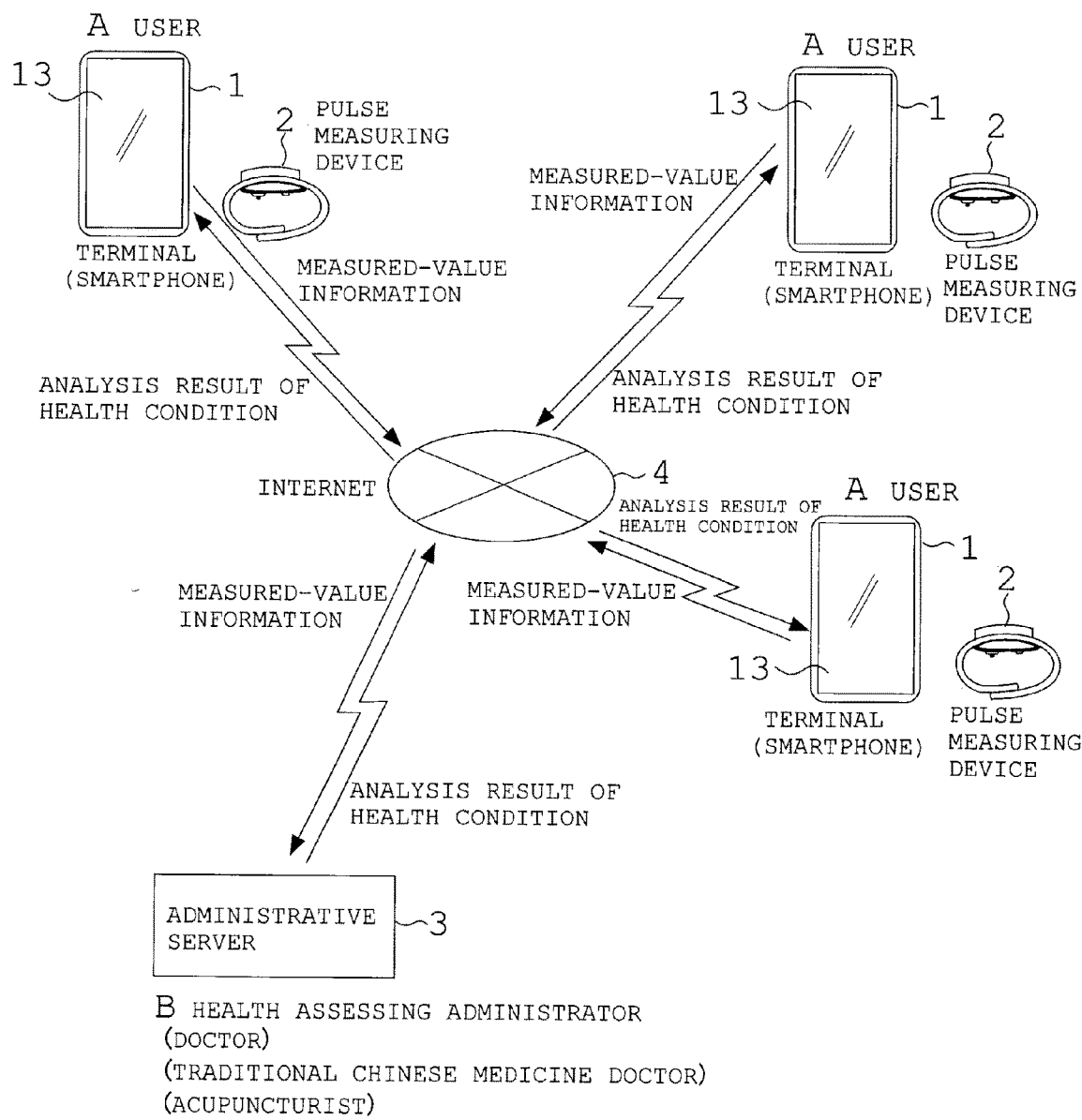
FIG. 1 is a schematic configuration diagram that illustrates a system that assesses health condition by measuring pulse according to an aspect of the present invention.

FIG. 1 is a schematic configuration diagram that illustrates a system that assesses health condition by measuring pulse according to an aspect of the present invention.

The system that assesses health condition by measuring pulse according to an aspect of the present invention includes terminals 1, such as smartphones, tablets, and personal computers, of users A who receive assessments of health condition (physical condition), pulse measuring devices 2a, 2b that measure various condition of pulse at wrists, and an administrative server 3 operated by a health assessing administrator B who uses measured-value data of the users A to assess health condition based on pulse. The health assessing administrator B is a doctor, or doctors belong to the health assessing administrator B. Traditional Chinese medicine doctors and experts who have deep knowledge in oriental medicine, such as acupuncturists desirably belong.

Each user A who wants to know health condition of the user A based on pulse diagnosis measures pulse and blood pressure of the user A with one of the pulse measuring devices 2a, 2b. The user A transmits measured values from one of the terminals 1 through the Internet 4 to the health assessing administrator B.

The health assessing administrator B who has received the measured values refers to the measured values, information on physical condition and health condition which have been preliminarily stored, such as an age and a sex of the user A, previously-measured-value data, pulse rates and blood pressures of healthy ordinary people, and pulse rates and blood pressures of ordinary people when ordinary people are unhealthy. The health assessing administrator B analyzes the referred information with the administrative server 3. The health assessing administrator B transmits current health condition of the user A that is an analysis result to the terminal 1 of the user A through the Internet 4.

The user A reads information on assessment of health condition displayed on a display unit 13 of the terminal 1, and knows physical condition and symptoms. In FIG. 1, the health assessing administrator B is one, and the users A are three. However, the number of the users A is not limited to three, and may naturally be other multiple numbers.

<Configuration of Pulse Measuring Device>

Figure 2A:
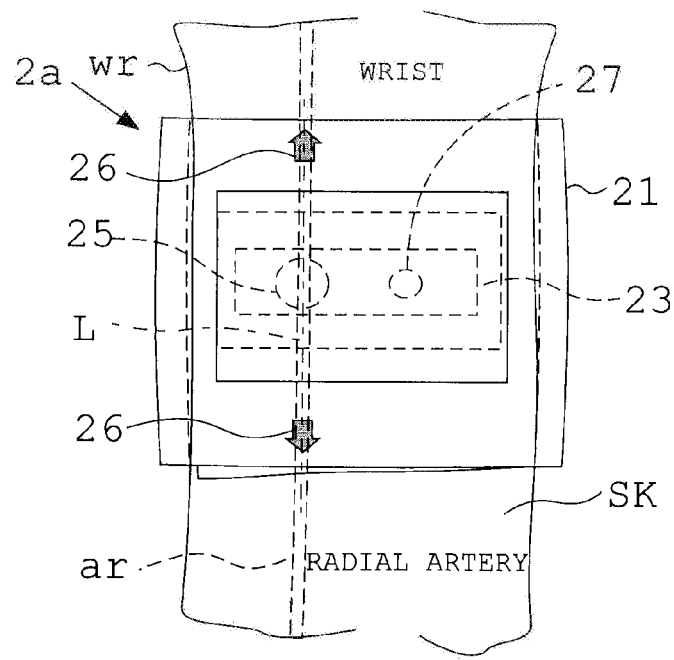
FIGS. 2A and 2B illustrate an example of a pulse measuring device worn around.
Figure 2B:
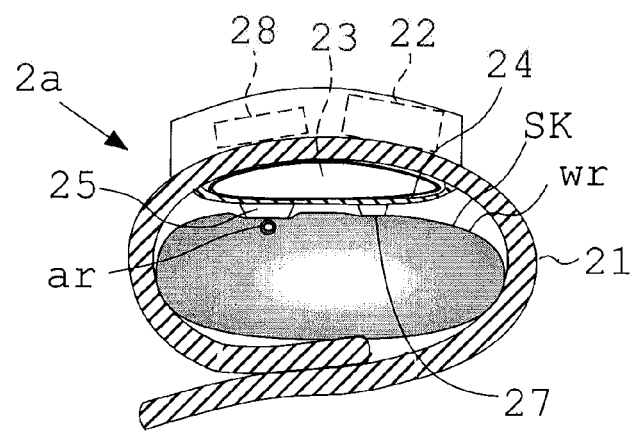

FIGS. 2A and 2B illustrate a basic shape of the pulse measuring device worn around. FIG. 2A is a front view. FIG. 2B is a side cross-sectional view.

For example, one of the users A uses one of the pulse measuring devices 2a worn around as illustrated in FIGS. 2A and 2B to measure pulse at a wrist wr of the user A. The pulse measuring device 2a includes a band 21 worn around a radial-artery portion ar of the wrist wr, for example, an airbag 23 inflated by air supplied by a pump 22 that is attached to the band 21, a guide sheet 24 that is attached to the airbag 23, is flexible, and has a curved shape, and a pressure sensor 25 that is in contact with skin, is disposed via the guide sheet 24 on the airbag 23, and measures pulse and blood pressure. The pressure sensor 25 is connected to a display circuit, and measured values (a pulse rate and a blood pressure) are displayed on a display unit. Further, the pressure sensor 25 transmits signals, and measured values (a pulse rate and a blood pressure) are displayed on the display unit 13 that is a monitor screen of the terminal 1, such as a smartphone, a tablet, or a personal computer. At this stage, the user A infers to some extent that the pulse rate and the blood pressure of the user A are not good.

Two arrows 26 are marked on a surface of the band 21 of the pulse measuring device 2a worn around. The two arrows 26 are for positioning. A line L that passes through the two arrows 26 passes through a central point of the pressure sensor 25. Due to the arrows 26, the pressure sensor 25 is in contact with a suitable position in the radial-artery portion ar of the wrist wr, and accurately measures pulse rate and blood pressure. That is, the arrows 26 allow a layman to perform measurement at a suitable position of an artery as similarly as an expert.

FIG. 3 is a flowchart that illustrates control in which a measurement-surface strength sensor of the pulse measuring device adjusts tightness of the band.

The pulse measuring device 2a worn around according to an aspect of the present invention includes a measurement-surface strength sensor 27 that measures strength of pressing force against a surface of skin sk of a wrist. A microcomputer 28 of the pulse measuring device 2a controls the measurement-surface strength sensor 27. The pressure sensor 25 measures pulse. The measurement-surface strength sensor 27 measures a state in which the pressure sensor 25 is in contact with a surface of skin sk of a wrist wr, that is a contact pressure. The measurement-surface strength sensor 27 adjusts tightness of the band 21 worn around a wrist wr by adjusting degree of filling of air into the airbag 23.

As illustrated in FIG. 12C, pulse slightly changes by ways of taking pulse. If pulse can be measured by a finger that slightly touches skin sk as in "fu pulse" or "fu taking", supply of air supplied to the airbag 23 is decreased to loosen tightness of the band 21 around a wrist. The measurement-surface strength sensor 27 measures strength of the tightness, and the microcomputer 28 gives a command to decrease supply of air supplied to the airbag 23.

Alternatively, if the band 21 needs to be strongly pressed against a wrist wr as in "chin pulse" or "chin taking", air supplied to the airbag 23 is increased. Tightness around a wrist wr is delicately changeable for a person to be measured. The measurement-surface strength sensor 27 performs measurement, and the microcomputer 28 gives a command to increase supply of air supplied to the airbag 23. The measurement-surface strength sensor 27 and the microcomputer 28 perform control to change supply of air supplied to the airbag 23.

A pulse type of a person changes within a physiological range by an age, a sex, a constitution, mental condition, circumstances at the time of measurement. For example, the younger an age is, the faster pulse is. A young man has a strong pulse. An aged person has a weak pulse. An elated person has a strong pulse. A hungry person has a weak pulse. Further, a person to be measured receives effect of change of seasons. The above microcomputer 28 of the pulse measuring device 2a exactly performs adjustment for such slight changes.

A pulse wave sensor (not shown) may be used instead of the pressure sensor 25. The pulse wave sensor includes an LED that emits light, and a photodetector that measures an amount of absorbed light that is changed by variation of a volume of a blood vessel. The pulse measuring device 2a is not limited to a configuration of the band 21 worn around illustrated in the drawings. Various configurations may be used for the pulse measuring device 2a as long as tightness around a wrist wr is changeable.

<Configuration of Individually-Measuring Pulse Measuring Device that Includes a Plurality of Pressure Sensors>

Figure 4A:
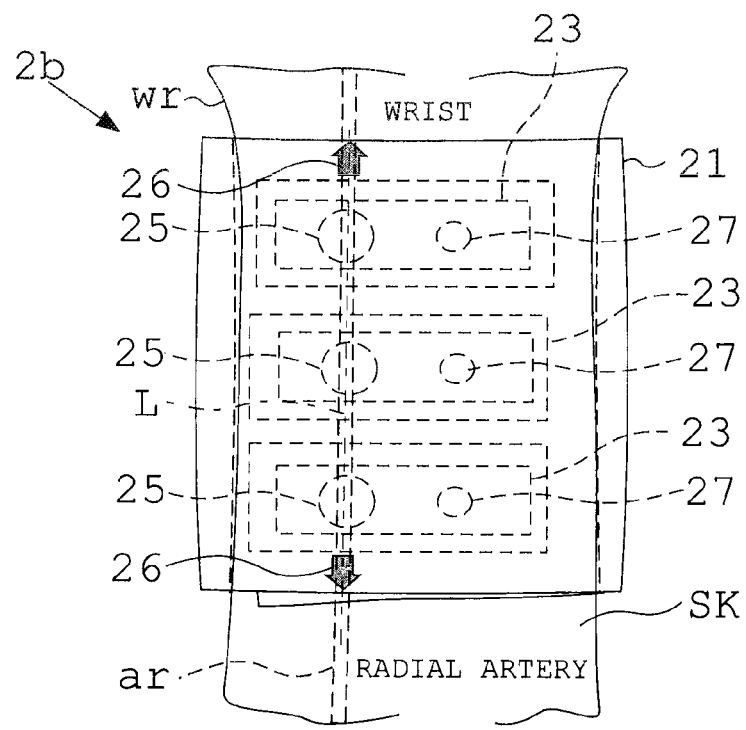
FIGS. 4A and 4B illustrate an individually-measuring pulse measuring device that includes a plurality of pressure sensors.
Figure 4B:
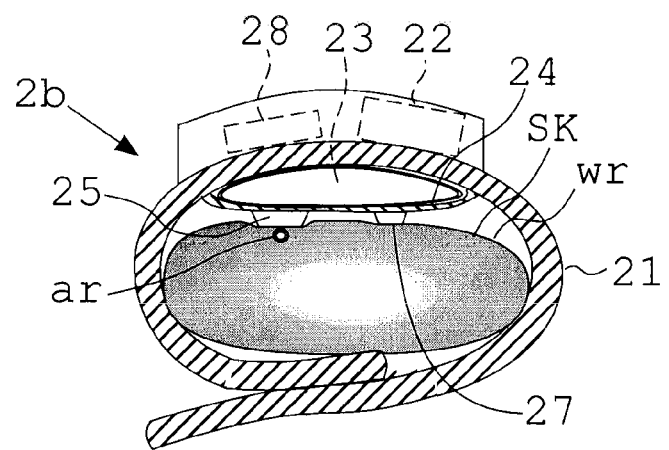

FIGS. 4A and 4B illustrate an individually-measuring pulse measuring device that includes a plurality of pressure sensors. FIG. 4A is a front view. FIG. 4B is a side cross-sectional view. In the description below, if a member has the same function as a member of the pulse measuring device 2a worn around, the member is designated the same reference numeral as the member of the pulse measuring device 2a worn around.

The individually-measuring pulse measuring device 2b illustrated in FIGS. 4A and 4B is a modification of pulse measuring device that includes a plurality of pressure sensors. A band 21 includes three pressure sensors 25 to individually measure pulse at three positions in a radial-artery portion ar: a "sun" position of a wrist wr near fingertips, a "kan" position next to the "sun" position, and a "shaku" position next to the "kan" position. The one band 21 includes three airbags 23, guide sheets 24 that are attached to the respective airbags 23, are flexible, and each have a curved shape, and pressure sensors 25 that are via the respective guide sheets 24 on the respective airbags 23. Further, the one band 21 includes measurement-surface strength sensors 27 near the respective pressure sensors 25.

FIGS. 4A and 4B exemplify the one band 21 that includes the three pressure sensors 25. The three pressure sensors 25 are not necessarily attached to the one band 21. The three pressure sensors 25 may be attached to three respective bands 21.

In the individually-measuring pulse measuring device 2b illustrated in FIGS. 4A and 4B, each measurement-surface strength sensor 27 performs measurement, and the microcomputer 28 gives command to increase or decrease supply of air supplied to each airbag 23. The measurement-surface strength sensors 27 and the microcomputer 28 perform control to change supply of air supplied to the airbags 23, and thus adjust tightness of each position where pulse is measured. Therefore, the individually-measuring pulse measuring device 2b measures slight variation in pulse.

Two arrows 26 are marked on a surface of the band 21 of the individually-measuring pulse measuring device 2b. Due to the arrows 26, the pressure sensors 25 are in contact with suitable positions in the radial-artery portion ar of a wrist, and each accurately measure pulse rate and blood pressure. Due to the arrows 26, the individually-measuring pulse measuring device 2b accurately measures pulse of the artery at three positions: the "sun" position, the "kan" position, and the "shaku" position that will be described below. Further, due to the arrows 26, the pressure sensors 25 are accurately pressed against and measure the "sun" position, the "kan" position, and the "shaku" position of an artery of a left wrist and an artery of a right wrist.

Figure 5:
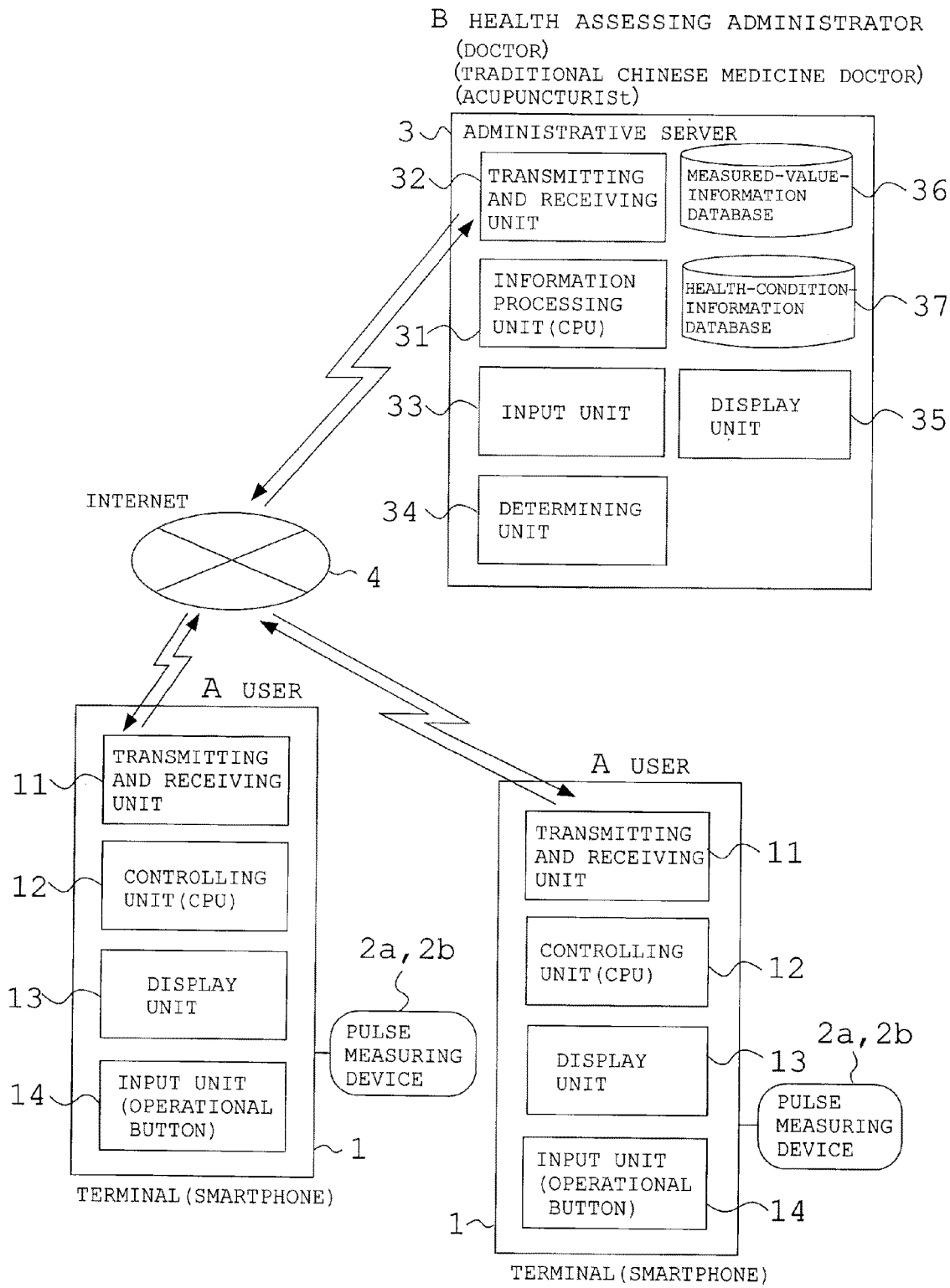
FIG. 5 is a block diagram that illustrates a configuration of a system that assesses health condition by measuring pulse.
Figure 6:
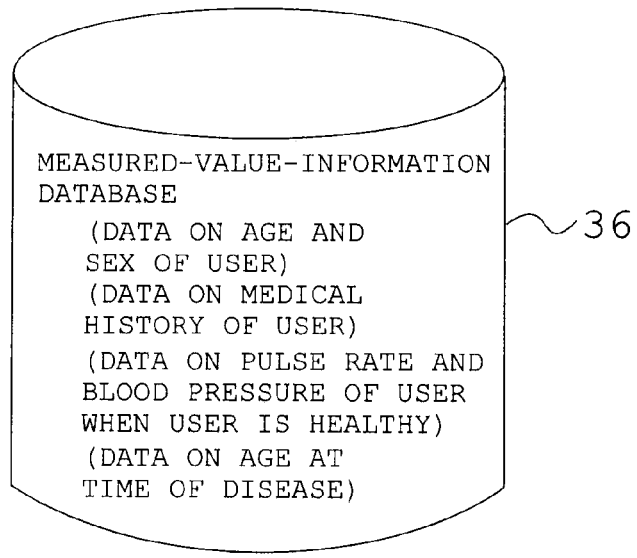
FIG. 6 is a block diagram that illustrates a concrete configuration of a measured-value-information database.
Figure 7:
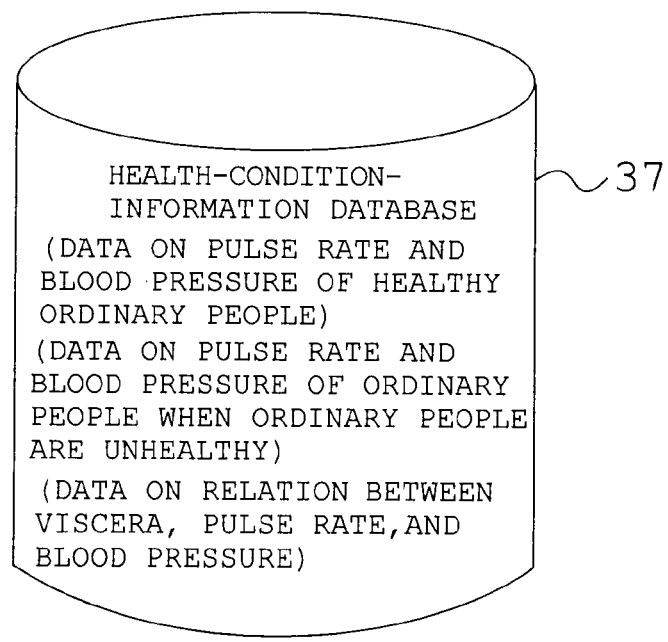
FIG. 7 is a block diagram that illustrates a concrete configuration of a health-condition-information database.

FIG. 5 is a block diagram that illustrates a configuration of a system that assesses health condition by measuring pulse. FIG. 6 is a block diagram that illustrates a concrete configuration of a measured-value-information database. FIG. 7 is a block diagram that illustrates a concrete configuration of a health-condition-information database.

Each terminal 1 is a device, such as a smartphone, a tablet, or a personal computer, that includes a transmitting and receiving unit 11 that mainly communicates with an administrative server 3 of a health assessing administrator B, and a controlling unit 12, such as a central processing unit (CPU). Each terminal 1 transmits to the administrative server 3 and receives from the administrative server 3 a pulse and a blood pressure of a user A measured with a pulse measuring device 2a or an individually-measuring pulse measuring device 2b. Further, each terminal 1 transmits to the administrative server 3 and receives from the administrative server 3 measured values of a user A, such as a body temperature, as necessary. A monitor screen of each terminal 1 functions as a display unit 13 that displays measured values, and health condition and physical condition that are analysis results of the measured values. The monitor screen (display unit 13) of each terminal 1 may display measured values, such as a pulse rate, a blood pressure, a body temperature, measured by a user A. The user A reads measured numerical values, and may know to some extent whether the measured numerical values are abnormal or not.

If a monitor screen (display units 13) of a terminal 1 is a touch panel, the monitor screen (display unit 13) functions as an input unit 14 that is used to input numerical values and addresses, for example. If a terminal 1 includes a keyboard or operational buttons, the keyboard or the operational buttons function (s) as an input unit 14.

If a terminal 1 includes a global-positioning-system (GPS) function, a position where a measurement is performed is pinpointed. Therefore, the terminal 1 is suitable for a system that assesses health condition according to an aspect of the present invention used during a disaster. The administrative server 3 determines whether a user A who wants to know health condition is in emergency or not. If the user A is in emergency, the administrative server 3 immediately transmits a request to call for an ambulance. The GPS allows transmission of position information.

If a terminal 1 is a smartphone that include a pulse wave sensor (photoelectric pulse-wave sensor) that is not shown, pulse is easily measured without a pulse measuring device 2a or an individually-measuring pulse measuring device 2b that has been described above. Pulse wave of the pulse wave sensor is variation of volume of a blood vessel generated by a heart that pumps blood. Pulse and the like are measured by making a pulse wave sensor touch a surface of a body. The pulse wave sensor is suitable to determine whether a user A is in an emergency in a stricken area.

<Configuration of Administrative Server>

A health assessing administrator B who assesses health condition by measuring pulse uses the administrative server 3. The administrative server 3 includes an information processing unit 31, such as a CPU, a transmitting and receiving unit 32, an input unit 33, a determining unit 34, and a display unit 35, as illustrated in FIG. 5. The administrative server 3 includes a measured-value-information database 36 that stores information on health condition of users A who receive assessments of health condition and, measured-value data on previous pulse, and a health-condition-information database 37 that stores variable factors of pulse and health-condition information on health condition.

As illustrated in FIG. 6, the measured-value-information database 36 that stores measured-value information on users A stores current ages and sexes of the users A, maximum and minimal pulse rates and maximum and minimal blood pressures of the users A when the users A are healthy, medical histories of the users A, ages at times of disease, and maximum and minimal pulse rates and maximum and minimal blood pressures of the users A at times of disease. A pulse rate varies in proportion to an age. Therefore, pulse rates that are normal for young people may be abnormal for aged people. A current age is an important factor. Further, maximum and minimal pulse rates and maximum and minimal blood pressures of healthy people are slightly different from each other, and thus are also important basic data.

Information on medical histories of users A is also an important factor because abnormal pulse often directly leads to a chronic illness. Ages at times of disease, and maximum and minimal pulse rates and maximum and minimal blood pressures of users A at times of disease are important data. Comparing maximum and minimal pulse rates when a person is healthy with maximum and minimal pulse rates of the person at times of disease and comparing maximum and minimal blood pressures when the person is healthy with maximum and minimal blood pressures of the person at times of disease allow easily determining whether current condition is healthy or not.

As illustrated in FIG. 7, the health-condition-information database 37 stores information data on relation between viscera, pulse rates at positions where pulse is measured, and maximum and minimal blood pressures of healthy ordinary people classified according to age, and information data on relation between viscera, pulse rates at positions where pulse is measured, and maximum and minimal blood pressures of ordinary people when ordinary people are unhealthy. If a user A does not have a medical history, there is no information data used for comparison. Comparing viscera, pulse rates at positions where pulse is measured, and maximum and minimal blood pressures of healthy ordinary people with viscera, pulse rates at positions where pulse is measured, and maximum and minimal blood pressures of ordinary people when ordinary people are unhealthy allows assessing whether a user A is healthy or not based on measured values of the user A.

The determining unit 34 of the administrative server 3 receives measured values of pulse measured by a pulse measuring device 2a or 2b from a terminal 1. If a condition for comparison of matters related to a user A with measured values is satisfied, the determining unit 34 compares the measured values with data stored in the measured-value-information database 36, and data stored in the health-condition-information database 37. Then the determining unit 34 assesses and infers health condition.

Based on numerical values of measured values shown in Tables 1 to 5 described below, the determining unit 34 assesses and infers current health condition of a user A, such as current physical condition and current disease condition.

Figure 8:
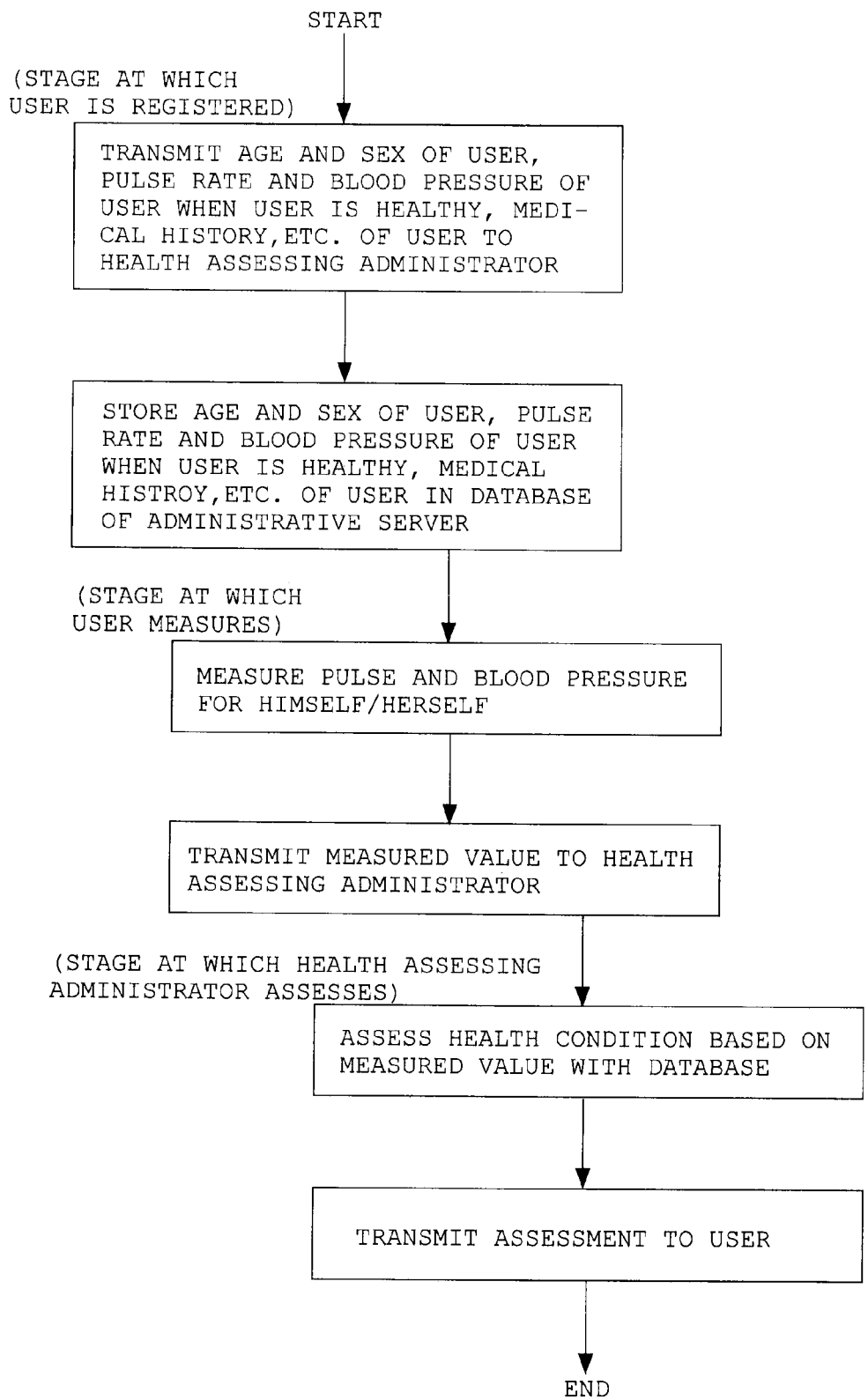
FIG. 8 is a process flowchart that illustrates a process procedure that assesses health condition by using a system that assesses health condition by measuring pulse according to an aspect of the present invention.

FIG. 8 is a process flowchart that illustrates a process procedure that assesses health condition by using a system that assesses health condition by measuring pulse according to an aspect of the present invention.

The process procedure that assesses health condition by using a system that assesses health condition by measuring pulse according to an aspect of the present invention will be described.

(1) Stage at which User is Registered

First, a user A who wants to receive an assessment of health condition accesses the administrative server 3 of a health assessing administrator B. The user A preliminarily stores in the measured-value-information database 36 of the administrative server 3 a current age and a sex of the user A, maximum and minimal pulse rates and maximum and minimal blood pressures of the user A when the user A is healthy, a medical history of the user A, ages of the user A at times of disease, and maximum and minimal pulse rates and maximum and minimal blood pressures of the user A at times of disease.

(2) Stage at which User Measures

When the user A wants to know health condition of the user A, the user A measures pulse and blood pressure with a pulse measuring device 2a or 2b at some positions in a radial-artery portion ar of wrists of the user A. Alternatively, the user A periodically measures pulse and blood pressure with the pulse measuring device 2a or 2b at some positions in a radial-artery portion ar of the wrists of the user A. The user A measures a body temperature as necessary. The user A transmits the measured values from a terminal 1, such as a smartphone, to an administrative server 3 of a health assessing administrator B.

(3) Stage at which Health Assessing Administrator Assesses

A determining unit 34 of the administrative server 3 of the health assessing administrator B compares measured-value data, such as a pulse rate and a blood pressure, transmitted from the user A with the measured-value-information database 36 of the administrative server 3 that stores data on previously-measured pulse of the user A, and the health-condition-information database 37 of the administrative server 3 that stores data on relation between unhealthy viscera and positions where pulse is measured. Consequently, an assessment and analysis of health condition of the user A is performed. The assessment information is transmitted to the terminal 1 of the user A from the administrative server 3 of the health assessing administrator B.

The user A knows health condition of the user A by reading assessment information displayed on the display unit 13 of the terminal 1. In this way, the user A receives an assessment of health condition from an expert at a remote place.

Analysis Example 1: "Fu Pulse" and "Chin Pulse"

Next, a concrete assessment operation that assesses health condition by using a system that assesses health condition by measuring pulse according to an aspect of the present invention will be described. Tables 1 to 5 are examples. Pulse diagnosis includes several dozens of health assessments and thus is not naturally limited to Tables 1 to 5.

If measured values of pulse transmitted from the user A are "fu pulse" or "chin pulse", for example, the determining unit 34 of the administrative server 3 of the health assessing administrator B performs analysis illustrated in Table 1. The fu pulse is felt by lightly pressing a finger against a radial artery. The fu pulse indicates condition in which a blood vessel relaxes, that is a condition in which a peripheral blood vessel expands and disease is at a surface. The health condition is for the purpose of radiation of heat from a body, and indicates suspicion of a "cold". A method that deals with the fu pulse is proposed.

TABLE 1

Relation between Depth of Pulse and Health Condition

| Type | Condition of pulse | Inferred health condition |
|---|---|---|
| Fu pulse | Condition in which blood vessel relaxes | Condition in which peripheral blood vessel expands, etc. |
| Hei pulse | Condition in which Fu pulse or Chin pulse is not identified | Good health condition |
| Chin pulse | Condition in which blood vessel becomes tight | Condition in which peripheral blood vessel contracts, etc. |

On the other hand, "chin pulse" is felt by strongly pressing a finger against a radial artery. Chin pulse indicates condition in which a blood vessel becomes tight, that is a condition in which a peripheral blood vessel contracts. It is thought that the cause is often the cold. To deal with the "chin pulse", it is proposed that body is not allowed to lose heat.

"Hei pulse" is not fu pulse nor chin pulse, and indicates good health condition.

Analysis Example 2: "Saku Pulse" and "Chi Pulse"

Figure 9:
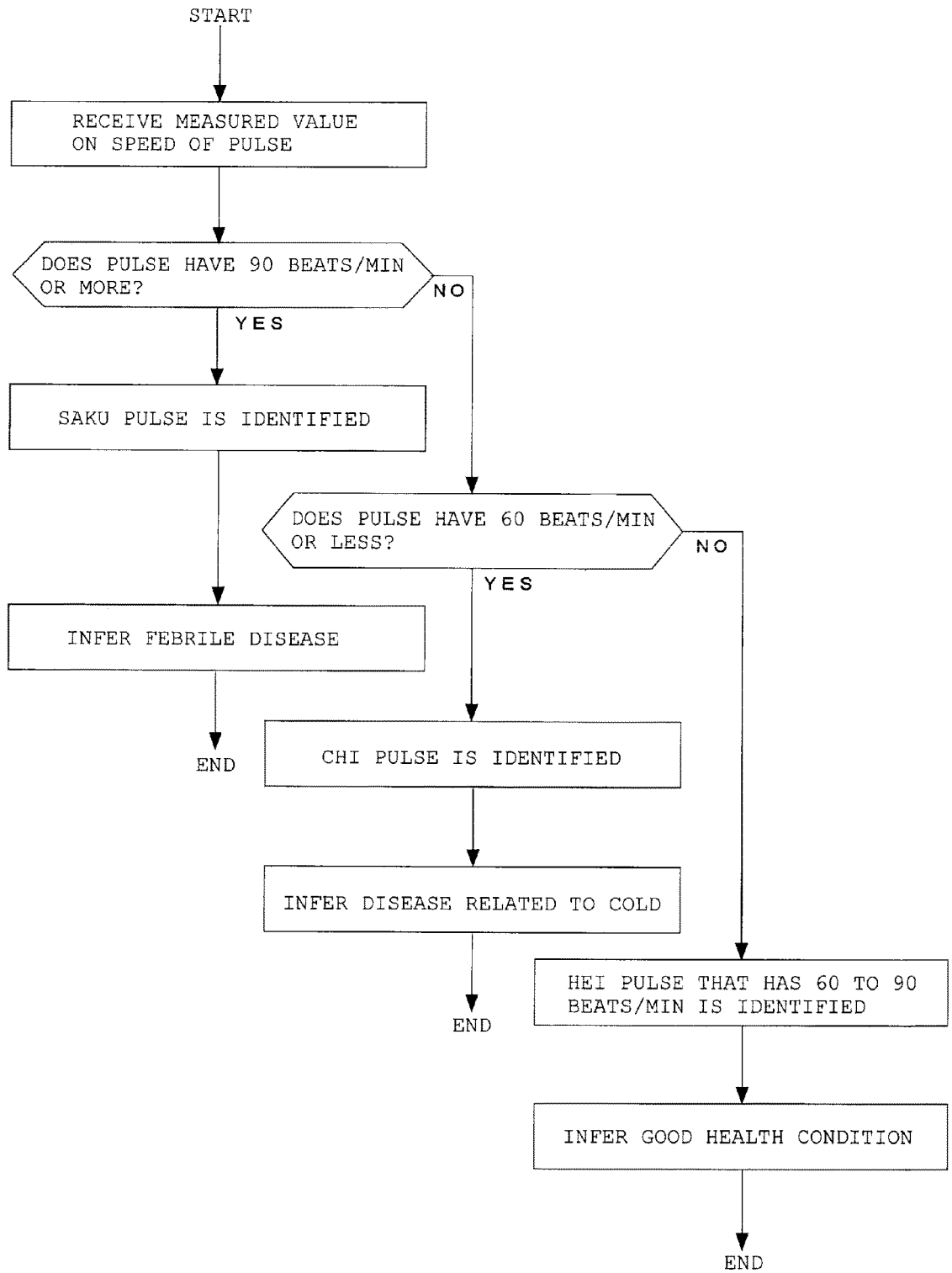
FIG. 9 is a flowchart that illustrates an analysis process method of "saku pulse" and "chi pulse"

FIG. 9 is a flowchart that illustrates an analysis process method of "saku pulse" and "chi pulse".

As illustrated in FIG. 9, if a result of measured pulse transmitted from a user A has 90 beats/minute or more, the determining unit 34 of the administrative server 3 determines that the pulse is "saku pulse". If pulse has 60 beats/minute or less, the determining unit 34 of the administrative server 3 determines that the pulse is "chi pulse". It is determined that other pulse is "hei pulse". The "saku pulse" and the "chi pulse" are analyzed as shown in FIG. 2.

TABLE 2

Relation between Speed of Pulse and Health Condition

| Type | Beats(min) | Inferred health condition |
|---|---|---|
| Saku pulse | 90 or more | Febrile disease, general infection, etc. |

TABLE 2-continued

Relation between Speed of Pulse and Health Condition

| Type | Beats(min) | Inferred health condition |
|---|---|---|
| Hei pulse | 60 to 90 | Good health condition |
| Chi pulse | 60 or less | Disease related to cold, hypothyroidism, etc. |

Note:
A person who has a fast or slow pulse rate by nature does not apply to the numerical values and is assessed according to a personal pulse rate.

The "saku pulse" or pulse that has 90 beats/minute or more indicates condition in which blood flow is fast, and condition in which basal metabolic rate increases. The "saku pulse" indicates suspicion of general infections, such as febrile illness, mental tension, hyperthyroidism, and dehydration. To deal with the "chin pulse", it is suggested that body heat is cooled.

On the other hand, the "chi pulse" or pulse that has 60 beats/minute or less indicates condition in which blood flow is slow, and condition in which basal metabolic rate decreases. For example, the "chi pulse" indicates suspicion of hypothyroidism or hypothermia.

In case of the "chi pulse", heart disease (atrioventricular block) is generally inferred. If a heart is normal, endocrine disease, such as hypothyroidism (bradycardia due to decrease in basal metabolic rate) is inferred. Further, ischemia (deficiency in blood) or kidney failure (deficiency in vigor) is inferred.

In case of "hei pulse", good health condition is inferred.

Analysis Example 3: "Jitsu Pulse" and "Kyo Pulse"

If a result of measured pulse transmitted from a user A is "jitsu pulse" or "kyo pulse", for example, the determining unit 34 of the administrative server 3 performs analysis as illustrated in Table 3. In case of the "jitsu pulse", a blood vessel is filled with blood, and blood applies pressure to the blood vessel. For example, the "jitsu pulse" indicates suspicion of high blood pressure, arteriosclerosis, and increase in cardiac output.

TABLE 3

Relation between Strength of Pulse and Health Condition

| Type | Blood pressure (Max/Min)mmHg | Inferred health condition |
|---|---|---|
| Jitsu pulse | 160/95 or more | High blood pressure, arteriosclerosis, etc. |
| Hei pulse | 70 to 80/120 to 130 | Good health condition |
| Kyo pulse | 100/60 or less | Low blood pressure, decrease in vitality, etc. |

Note:
A person who has a high or low blood pressure by nature does not apply to the numerical values and is assessed according to a personal blood pressure.

The "kyo pulse" is obviously weak, and thus is hardly felt in the "fu pulse", the "hei pulse", and the "chin pulse". In case of the "kyo pulse", blood barely fills a blood vessel, and a pressure is not sufficient in the blood vessel. Therefore, the "kyo pulse" indicates low blood pressure. Further, the "kyo pulse" indicates decrease in vitality.

Analysis Example 4: "Sun" Position, "Kan" Position, and "Shaku" Position

Figure 10:
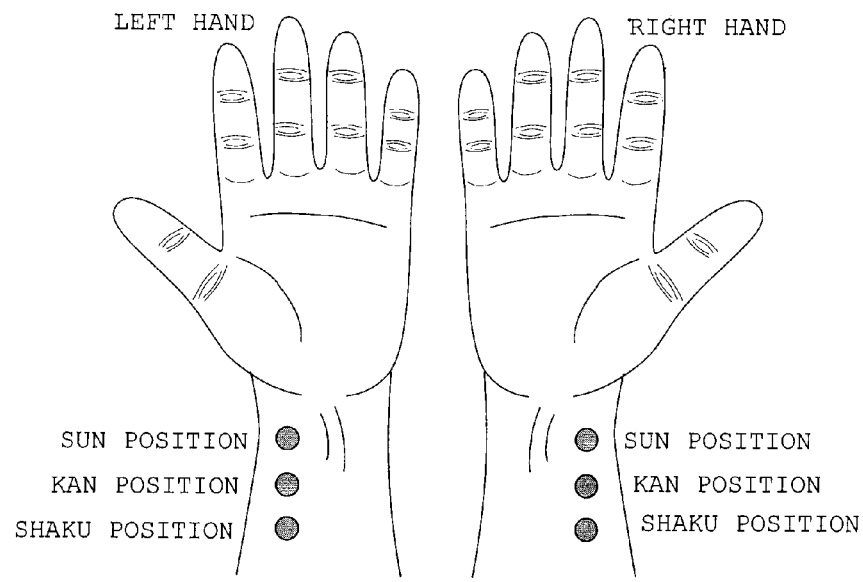
FIG. 10 is a schematic explanation view that illustrates a "sun" position, a "kan" position, and a "shaku" position of wrists.

FIG. 10 is a schematic explanation view that illustrates the "sun" position, the "kan" position, and the "shaku" position of wrists.

Figure 11:
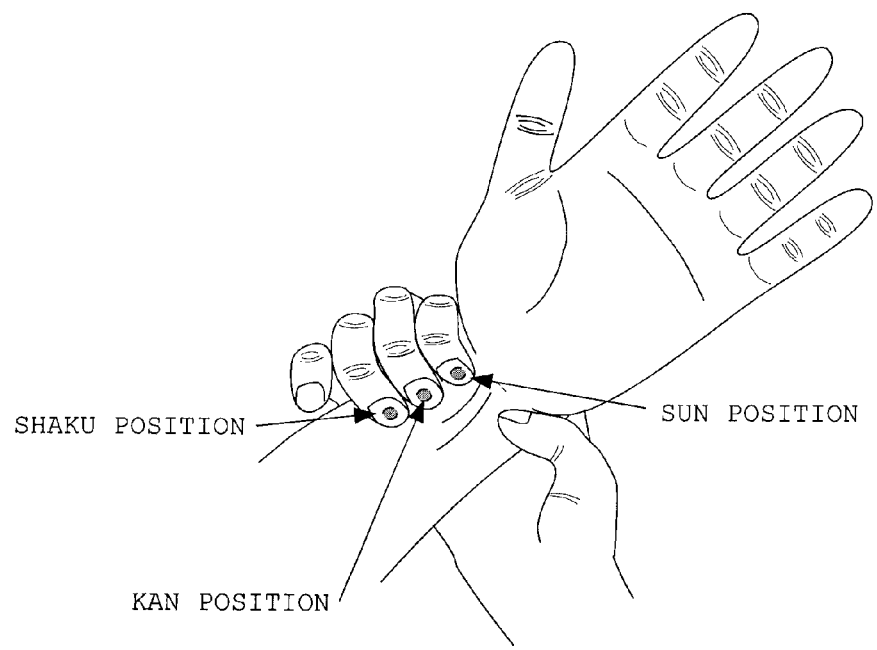
FIG. 11 is a schematic explanation view that illustrates a measurement method of pulse diagnosis of oriental medicine in which a forefinger, a middle finger, and a ring finger are pressed against an artery of a left wrist.

If a result of measured pulse transmitted from a user A also includes differences between the "sun" position, and the "kan" position, and the "shaku" position, the determining unit 34 of the administrative server 3 performs analysis as illustrated in Tables 4 and 5. As illustrated in FIG. 11, health condition of human viscera, especially condition of five viscera (heart, liver, spleen, lung, and kidney) is inferred based on pulse at positions on left and right wrists where fingers touch.

As shown in Table 4, condition of a heart and a small intestine is inferred based on pulse at the "sun" position of an artery of a left hand. The "sun" position is the nearest to fingertips. Condition of a liver and a gallbladder is inferred based on pulse at the "kan" position next to the "sun" position. Condition of a kidney and a bladder is inferred based on pulse at the "shaku" position next to the "kan" position.

As shown in Table 5, condition of a lung and a large intestine is inferred based on pulse at the "sun" position of an artery of a right hand. The "sun" position is the nearest to fingertips. Condition of a spleen and a stomach is inferred based on pulse at the "kan" position next to the "sun" position. Condition of a viscus near the kidney (vigor of the kidney (san shou)) is inferred based on pulse at the "shaku" position next to the "kan" position.

TABLE 4

Relation between Left Hand Pulse and Corresponding Viscera

| Left Hand | Measured Position | Corresponding viscera |
|---|---|---|
| SUN POSITION | Wrist(position that corresponds to forefinger) | Heart, small intestine |
| KAN POSITION | Wrist(position that corresponds to middle finger) | Liver, gallbladder |
| SHAKU POSITION | Wrist(position that corresponds to ring finger) | Kidney, bladder |

TABLE 5

Relation between Right Hand Pulse and Corresponding Viscera

| Right Hand | Measured Position | Corresponding viscera |
|---|---|---|
| SUN POSITION | Wrist(position that corresponds to forefinger) | Lung, large intestine |
| KAN POSITION | Wrist(position that corresponds to middle finger) | Spleen, stomach |
| SHAKU POSITION | Wrist(position that corresponds to ring finger) | Vigor of kidney(san shou) |

A lung and a heart are at a chest over a diaphragm. A stomach, a spleen, and a liver are at a middle of a trunk, that is over an abdomen. A kidney is at a lower part of the abdomen. The heart corresponds to pulse at a position near fingertips of a left hand. The lung corresponds to pulse at a position near fingertips of a right hand. The liver corresponds to pulse at a central position of a left hand. The spleen and the stomach correspond to pulse at a central position of aright hand. The kidney corresponds to pulse at a position near an elbow of a left hand. The san shou corresponds to pulse at a position near an elbow of a right hand. Five of six fingers that are used to measure pulse correspond to five viscera. One finger is too many. The one finger is balanced by the san shou that is a traditional-Chinese-medical organ. A left kidney is a kidney and a right kidney is the san shou. The san shou represents vigor and thermal energy of a kidney.

Positions of viscera that correspond to the "sun" position, the "kan" position, and the "shaku" position of a left hand, and the "sun" position, the "kan" position, and the "shaku" position of a right hand, and the analysis result of condition of the "fu pulse" and the "chin pulse" described above are used in combination. Consequently, measured values of pulse are assessed. Consequently, health condition is accurately assessed.

The present invention is not limited to the above embodiments, and modification is possible without departing from the scope of the present invention, as long as "pulse diagnosis" that has been performed by traditional Chinese medicine doctors or experts, such as acupuncturists by performing touch diagnosis is performed with a pulse measuring device and database analysis, and thus health condition is accurately assessed and health care is performed, and health condition is assessed based on both the assessment of health condition and general health checkup, and thus health care is contributed to.

A system that assesses health condition by measuring pulse and a method of operating the same according to an aspect of the present invention is used to personally assess health condition, and is used to assess whether victims in a stricken area are in emergency or not.

What is claimed is:

1. A system that assesses a health condition of a user, comprising:
    a pulse measuring device that measures pulse and blood pressure at an artery of the user;
    a terminal including a display unit that displays measured-value data corresponding to at least one of the pulse and blood pressure measured by the pulse measuring device, a controlling unit controlled by operating an input unit, and a transmitting and receiving unit; and
    an administrative server including a transmitting and receiving unit that receives the measured-value data transmitted from the transmitting and receiving unit of the terminal, a measured-value-information database that stores data on previously-measured pulse of the user, a health-condition-information database that stores data on relation between unhealthy viscera and positions where pulse is measured, and a determining unit that analyzes the health condition of the user, wherein
    the terminal is configured to allow the user to transmit the measured-value data from the terminal to the health assessing administrator,
    the administrative server is configured to transmit assessment information on the health condition of the user analyzed by the administrative server to the terminal,
    the pulse measuring device includes:
        a band adapted to be worn around a portion that corresponds to a radial-artery portion on a wrist;
        three airbags inflated by air supplied by a pump attached to the band, each of the three airbags extending laterally over the radial-artery portion on the wrist;
        guide sheets attached to the respective airbags, each of the guide sheets having a curved shape;
        pressure sensors measuring the pulse of the user, each of the pressure sensors being disposed via each of the respective guide sheets on each of the respective airbags, each of the pressure sensors being disposed below the respective one of the airbags to contact the radial-artery portion of the wrist; and measurement-surface strength sensors measuring a strength of a pressing force that presses the respective pressure sensors against a surface of the wrist, each of the measurement-surface strength sensors being disposed separate from and adjacent to the respective one of the pressure sensors, laterally from the radial-artery portion on the wrist, and below the respective one of the three airbags, and three positions in the radial-artery portion of the wrist, including a "sun" position near fingertips, a "kan" position next to the "sun" position, and a "shaku" position next to the "kan" position, are individually measured.

2. The system that assesses health condition by measuring pulse according to claim 1, wherein the measured-value-information database of the administrative server stores measured- information data on a current age of the user, maximum and minimal pulse rates and maximum and minimal blood pressures of the user when the user is healthy, a medical history of the user, an age of the user at a time of disease, and maximum and minimal pulse rates and maximum and minimal blood pressures of the user at the time of disease, and the health-condition-information database of the administrative server stores information data on relation between viscera, pulse rates at positions where pulse is measured, and maximum and minimal blood pressures of healthy ordinary people classified according to age, and information data on relation between viscera, pulse rates at positions where pulse is measured, and maximum and minimal blood pressures of ordinary people when ordinary people are unhealthy.

3. The system that assesses health condition by measuring pulse according to claim 1, wherein the pulse measuring device is configured so that the measurement-surface strength sensors that are disposed near the respective pressure sensors and measure strength of pressing force that presses the respective pressure sensors against a surface of the skin of the wrist each measure a difference between "fu pulse" felt by lightly pressing a finger against a radial artery and "chin pulse" felt by strongly pressing a finger against a radial artery.

4. The system that assesses health condition by measuring pulse according to claim 3, wherein two arrows are marked on a surface of the band of the pulse measuring device, and a central portion of the pressure sensor is on a line that passes through the two arrows.

5. The system that assesses health condition by measuring pulse according to claim 1, wherein two arrows are marked on a surface of the band of the pulse measuring device, and a central portion of the pressure sensor is on a line that passes through the two arrows.

6. A method of operating a system that assesses a health condition of a user, the method comprising:

measuring pulse and blood pressure of an artery of the user with a pulse measuring device, the pulse measuring device including a band adapted to be worn around a portion that corresponds to a radial-artery portion on a wrist, three airbags inflated by air supplied by a pump attached to the band, each of the three airbags extending laterally over the radial-artery portion on the wrist, guide sheets attached to the respective airbags, pressure sensors measuring the pulse of the user, each of the pressure sensors being disposed via each of the respective guide sheets on each of the respective airbags, each of the pressure sensors being disposed below the respective one of the airbags to contact the radial-artery portion of the wrist, and measurement-surface strength sensors measuring a strength of a pressing force that presses the respective pressure sensors against a surface of the wrist, each of the measurement- surface strength sensors being disposed separate from and adjacent to the respective one of the pressure sensors, laterally from the radial-artery portion on the wrist, and below the respective one of the three airbags;

transmitting measured-value data corresponding to at least one of the pulse and blood pressure measured by the pulse measuring device from a terminal to an administrative server comparing, by means of a determining unit, the measured-value data transmitted from the the terminal with a measured-value-information database of the administrative server that stores data on previously-measured pulse of the user, and a health-condition-information database of the administrative server that stores data on relationships between unhealthy viscera and positions where the pulse is measured;

analyzing the health condition of the user by the administrative server to generate an analysis result including a suspicion of general infections, including at least one of a febrile illness, a mental tension, a hyperthyroidism, and a dehydration, being identified when the measured-value data includes the measured pulse of the user being 90 beats/minute or more, or a suspicion of hypothyroidism or hypothermia being identified when the measured- value data includes the measured pulse of the user being 60 beats/minute or less; and transmitting the analysis result of the health condition of the user to the terminal.

7. The method of operating a system according to claim 6, wherein the analysis result further includes an abnormality in a heart and a small intestine is identified when the measured-value data includes the measured pulse of the user having an abnormality of an artery of a left wrist at a "sun" position near fingertips, an abnormality in a liver and a gallbladder is identified when the measured-value data includes the measured pulse of the user having an abnormality of the artery of the left wrist at a "kan" position next to the "sun" position, an abnormality in a kidney and a bladder is identified when the measured-value data includes the measured pulse of the user having an abnormality of the artery of the left wrist at a "shaku" position next to the "kan" position, an abnormality in a lung and a large intestine is identified when the measured-value data includes the measured pulse of the user having an abnormality of an artery of a right wrist at the "sun" position, an abnormality in a spleen and a stomach is identified when pulse of the measured-value data includes the measured pulse of the user having an abnormality of the artery of the right wrist at the "kan" position, and an abnormality in a viscus near the kidney is identified when the measured-value data includes the measured pulse of the user having an abnormality of the artery of the right wrist at the "shaku" position.

* * * * *